(12) United States Patent
Hall et al.

(10) Patent No.: US 6,218,105 B1
(45) Date of Patent: Apr. 17, 2001

(54) HIGH THROUGHPUT PAPILLOMA VIRUS IN VITRO INFECTIVITY ASSAY

(76) Inventors: Kathleen S. Hall, 273B Orion Way, Stateline, NV (US) 89449; Lloyd H. Smith, 1309 Aspen Pl., Davis, CA (US) 95616

( * ) Notice: Subject to any disclaimer, the term of this patent is extended or adjusted under 35 U.S.C. 154(b) by 0 days.

(21) Appl. No.: 09/479,825

(22) Filed: Jan. 7, 2000

Related U.S. Application Data

(63) Continuation-in-part of application No. 08/684,370, filed on Jul. 19, 1996, now abandoned.
(60) Provisional application No. 60/115,220, filed on Jan. 8, 1999.

(51) Int. Cl.[7] .............................. C12Q 1/68; C12Q 1/70; C12P 19/34
(52) U.S. Cl. .................... 435/5; 435/6; 435/7.1; 435/7.2; 435/7.21; 435/91.2; 435/91.32; 435/91.33; 435/91.51; 435/325; 435/366; 435/371
(58) Field of Search .............................. 435/5, 6, 7.1, 7.2, 435/7.21, 91.2, 325, 366, 371, 377, 91.51, 91.32, 91.33

(56) References Cited

U.S. PATENT DOCUMENTS 5,786,208 * 7/1998 Clark et al. ..................... 430/270

OTHER PUBLICATIONS

Smith et al., J. Invest. Dermatology, vol. 105, No. 3, pp. 438–444, Sep. 1995.*

* cited by examiner

Primary Examiner—David Guzo
(74) Attorney, Agent, or Firm—Robert C. Hall; Bozicevic, Field & Francis, LLP

(57) ABSTRACT

A high throughput virus in vitro infectivity assay method comprising growing cells in a multi-well format, infecting the cells with intact virion incubated with a test agent, and measuring expression of at least one viral nucleic acid sequence in the cells. The method also preferably comprises incubating intact virion without test agent to define a control. The cells are preferably human keratinocyte cells grown in monolayers. The viral nucleic acid sequence will generally comprise viral mRNA. In one preferred embodiment, the intact virion comprise Human Papilloma Virus, and more preferably Human Papilloma Virus-11. Measuring expression is generally carried out by releasing the viral mRNA from the cells by lysis, amplifying the mRNA as CDNA via RT-PCR, and detecting amplicons with specific probes. Cell lysis may be carried out by heating or by treatment with detergent.

12 Claims, 5 Drawing Sheets

HPV-11 in vitro Infectivity Assay

HPV-11 Neutralization & Inhibition

HPV infection of monolayer cells
Test antiviral agents for viral inhibition effectiveness

Extraction-less mRNA procedure

Method 1: Trypsinization/cellular lysis by heat

Method 2: Cellular lysis by detergent

RT-PCR of HPV-11 E2 mRNA

Primer/probe design utilizes intron/exon splice site

RT-PCR is carried out in one tube

PCR conditions are optimized for preferential amplification of E2 cDNA vs. genomic DNA by utilizing a short extension time.

Detection of HPV-11 E2 amplicons

Method 1: Ethidium bromide/agarose gel electrophoresis.

Method 2: ELISA Detection

Method 3: Real-time RT-PCR.

Method 4: Fluorescence detected of HPV-11.

Fig. 2

| Virus Dilution | $10^{-3}$ | $5 \times 10^{-4}$ | $10^{-4}$ | $10^{-5}$ | $10^{-6}$ | $10^{-7}$ | $10^{-8}$ | $10^{-9}$ |
|---|---|---|---|---|---|---|---|---|
| O.D. | 0.588 | 0.369 | 0.400 | 0.213 | 0.105 | 0.035 | 0.030 | 0.00 |
| Ct | 33 | 36 | 38 | 43 | 50 | 50 | 50 | 45 |

Fig.3B

HIGH THROUGHPUT PAPILLOMA VIRUS IN VITRO INFECTIVITY ASSAY

CROSS-REFERENCE TO RELATED APPLICATIONS

This is a continuation-in-part application of a co-pending U.S. patent application Ser. No. 08/684,370, filed Jul. 19, 1996, abandoned. This application also claims priority of U.S. provisional application Ser. No. 60/115,220, filed Jan. 8, 1999.

BACKGROUND OF THE INVENTION

1. Field of Invention

This invention relates to a high-throughput in vitro method of testing antiviral activity of various agents. More specifically, it describes a method of testing effectiveness of anti-papilloma virus agents which act early in the infection process. The method is useful in testing effectiveness of existing and potential antiviral drugs, including the efficacy of vaccines, in particular, future drugs directed to treatment of human papilloma virus infections.

2. Description of the Background Art

Cervical cancer is strongly linked to human papilloma virus (HPV) infection. HPV types 6 and 11 are associated with condylomata and low grade dysplasia while HPV-16 and -18 are associated with high grade dysplasia and cervical cancer. Information on the human immune response against Human papilloma viruses (HPV) predominantly comes from serological studies that used enzyme-linked immunosorbent assays (ELISA) targeted against HPV antigens. The simple detection of anti-HPV antibodies, however, fails to identify neutralizing antibodies (N-Abs) against HPV. Thus it has been widely recognized that only the detection of specific N-Abs against HPV will identify an effective immune response (protective antibodies). See, e.g., Foster et al., *Papillomavirus Report* 8,127–131 (1997).

Testing of the antiviral effectiveness of the new and existing agents against human papillomavirus are still performed in the in vivo testing involving use of laboratory animals and human subjects. These studies are expensive, time consuming and altered by individual differences among subjects.

A demonstration of efficacy prior to in vivo animal model testing would limit the candidate in vivo agents to the ones with increasing potential for in vivo effectiveness. This is especially important for those newer, more speculative agents for which purer antiviral effects are lacking. In vitro demonstration of efficacy can support a decision for expensive testing in animal model systems. In vitro studies are also useful for exploring drug-virus interactions which are awkward or infeasible in whole animal systems. In vitro testing offers the following advantages: 1) preliminary data on efficacy; 2) rapid turn around time; 3) economy; 4) ability to precisely control environmental conditions; 5) elimination of pharmacokinetics and variability of whole animal systems; and 6) small amounts of drugs are required.

There have been some encouraging developments, elsewhere and in our laboratory, for in vitro papillommavirus testing. Broker's laboratory has recently suggested that the xenograft system, which we originated, might be useful for antiviral testing (S. Dollard, et al., 1992, Gene Dev., 6:1131–1142).

In the Broker approach, fragments of HPV-11 infected human foreskin tissue is excised from the papillomatous cysts, growing beneath the renal capsule, and the fragments are placed onto a collagen gel "raft" culture. HPV-11 replication continues in the tissue fragment, as cells migrate laterally across the surface of the gel. We have explored the use of this system as a possible target for antiviral testing, and we have found that there is a high degree of regional variability in the extent of cell migration, tissue growth, and HPV-11 replication. This in vitro system, however, does not appear to be sufficiently consistent or precise to form a basis for tests. Further, since preliminary xenografts are required, the cost of the test includes the preliminary growth for three months, so some of the theoretical advantages of in vitro tests, economy and rapid turnaround are lacking.

Another in vitro system with potential was described by Laimins' group (Meyers, et al., 1992, Science, 257:971–973). In this system, human cervical cells, bearing HPV-31*b* episomal DNA are placed on collagen gel raft cultures and biosynthesis of complete virions occurs in the differentiating cells. It seems likely that this system may also be disadvantageously affected by regional variability.

Many of the disadvantages of the prior art methods of testing antiviral activity are overcome by the method of the present invention which precisely measures antiviral activity without the interferences of the regional variability, since the cell cultures are evenly dispersed monolayers.

Other in vitro methods have appeared in recent years but only one assay utilizes infectious virion. See, e.g., Smith et al., *J Invest Dermatol* 105, 438–444 (1995). Most vaccines and anti-viral agents to date prevent infection in the early stages of infection, i.e. binding to viral coat proteins, inhibition of viral nucleic to acids form entering the cellular nucleus or preventing RNA transcription. By using intact virion the infection of monolayers more closely mimics a true viral infection than the use of puesdo-virion. This in vitro PV assay relies on methods not conducive to high throughput screening. Past methodology required the isolation of RNA before RT-PCR could be performed to detect HPV mRNA expression within infected cells. Also nested set PCR was necessary for the detection of viral mRNA which is cumbersome in a high throughput method.

There is accordingly a need for an in vitro assay utilizing infectious virion which is amenable to use with high-throughput techniques. The present invention satisfies this need, as well as others, and generally overcomes the deficiencies found in the background art.

SUMMARY OF THE INVENTION

The present invention is a in vitro assay which allows for large scale screening of antiviral agents, in particular, human neutralizing antibodies against HPV-11. The invention can also be used for other viral HPV types such as -16, -18 and 31 as well as other viruses. This HT-RT-PCR HPV in vitro infectivity assay facilitates serologic studies on the response to HPV-11 infection and document the presence of neutralizing antibodies in the serum of and/or cervicovaginal secretions of patients with clinical HPV-related disease. The assay of the invention can also be utilized to screen numerous anti-viral candidates other than neutralizing antibodies. This invention can further be applied to the high throughput screening of specific cellular mRNA transcripts.

The invention, in general terms, comprises growing cells in a multi-well format, infecting the cells with intact virion incubated with a test agent, and measuring expression of at least one viral nucleic acid sequence in said cells. The method also preferably comprises incubating intact virion without test agent to define a control. The cells are preferably human keratinocyte cells grown in monolayers. The viral nucleic acid sequence will generally comprise viral mRNA. In one preferred embodiment, the intact virion comprise Human Papilloma Virus, and more preferably Human Papilloma Virus -11. Measuring expression is generally carried out by releasing the viral mRNA from the cells by lysis, amplifying the iRNA as cDNA via RT-PCR, and detecting amplicons with specific probes. Cell lysis may be carried out by heating or by treatment with detergent.

By way of example, and not necessarily of limitation, epithelial cells are grown in monolayers in multi-well tissue culture plates and then subjected to infectious HPV-11 virion. To detect neutralizing antibodies (antiviral effectiveness), test serum is added to HPV-11 virion prior to addition to the cells. Failure to detect HPV infection is indicative of neutralizing antibodies. The infected cells (with and without antiviral agents) are allowed to grow to confluency and then target mRNA is obtained by an extraction-less method.

The extraction-less method either involves trypsinization of the infected cells followed by cell lysis by heat or direct cell lyses by detergent solution. An aliquot of cell lysate are directly placed into multi-well PCR plates for one-tube RT-PCR.

The crude lysate is then subjected to RT-PCR under conditions which preferentially amplify the specific cDNA target rather than genomic DNA. The target mRNA contains a splice site which is utilized in primer and probe design. The target MRNA also has an exon size large enough to optimize PCR elongation times for the preferential amplification of the shorter cDNA.

Amplified HPV RT-PCR products can be detected quantitatively using different methods; gel electorphoresis, utilization of an internal HPV-11 DNA capture probe coupled to an ELISA, fluoresecent primers and biotinylated primers captured on streptavidn plates or via solid phase RT-PCR and real-time PCR utilizing a specific PV fluorogenic probe. A host cell transcript is also detected to be used as an internal mRNA internal control.

The HPV-11 in vitro infectivity assay detects RT-PCR products of the HPV-11 E2 transcript, which has increased the quantitative capabilities compared to previous in vitro assays which utilized nested set PCR. This HT-HPV in vitro infectivity assay could potentially be utilized in screening for protective immunity in ongoing clinical HPV vaccine trials. FIG. 1 illustrates the HT-RT-PCR-HPV-11 in vitro infectivity assay and the detection of neutralizing antibodies.

An object of the invention is to provide a method for the detection of anti-viral agents via high throughput screening.

Another object of the invention is to provide a method for detection of anti-viral agents which utilizes intact virion.

Another object of the invention is to provide a method for detection of anti-viral agents which does not require the isolation of RNA from DNA before performing RT-PCR.

Another object of the invention is to provide a method for detection of anti-viral agents which is easy and time efficient.

Another object of the invention is to provide a method for detection of anti-viral agents which requires small amounts of cells and test reagents.

Another object of the invention is to provide a method for detection of anti-viral agents which decreases the possibility of cross contamination by avoiding use of nested set PCR.

Another object of the invention is to provide a method for detection of anti-viral agents which eliminates the need for separate reaction vessels for RT and PCR.

Another object of the invention is to provide a method for detection of anti-viral agents which allows for quantitative analysis of HPV antiviral agents, and in particular, neutralizing antibodies, by eliminating nested set PCR and analyzing RT-PCR products with detection methods which allow numeric representation of the amount of RT-PCR amplification.

Further objects and advantages of the invention will be brought out in the following portions of the specification, wherein the detailed description is for the purpose of fully disclosing the preferred embodiment of the invention without placing limitations thereon.

BRIEF DESCRIPTION OF THE DRAWINGS

FIG. 2 is a flow chart illustrating generally the method of the high throughput RT-PCR HPV in vitro infectivity assay of the invention.

FIG. 3B is a chart illustrating the results for the ELISA and real-time RT-PCR detection methods for the corresponding viral dilutions represented in FIG. 3A. An Akaline phosphatase labeled probe for HPV-11 E2 was hybridized to E2 amplicons followed by the addition of p-nitrophenyl phosphate for the ELISA colorimetric detection of HPV-11 infection. The FAM/TAMRA "taqman probe" for E2 amplicons was utilized to detect Ct values in real-time RT-PCR.

DETAILED DESCRIPTION OF THE PREFERRED EMBODIMENTS

Figure 1A:
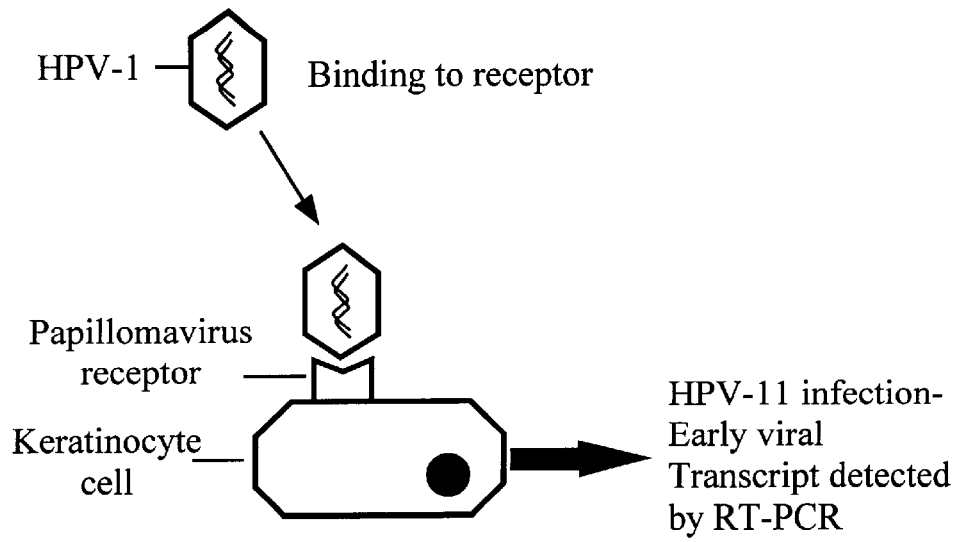
FIG. 1A is a diagrammatic depiction of the general aspects of a high throughput HPV in vitro infectivity assay in accordance with the present invention.
Figure 1B:
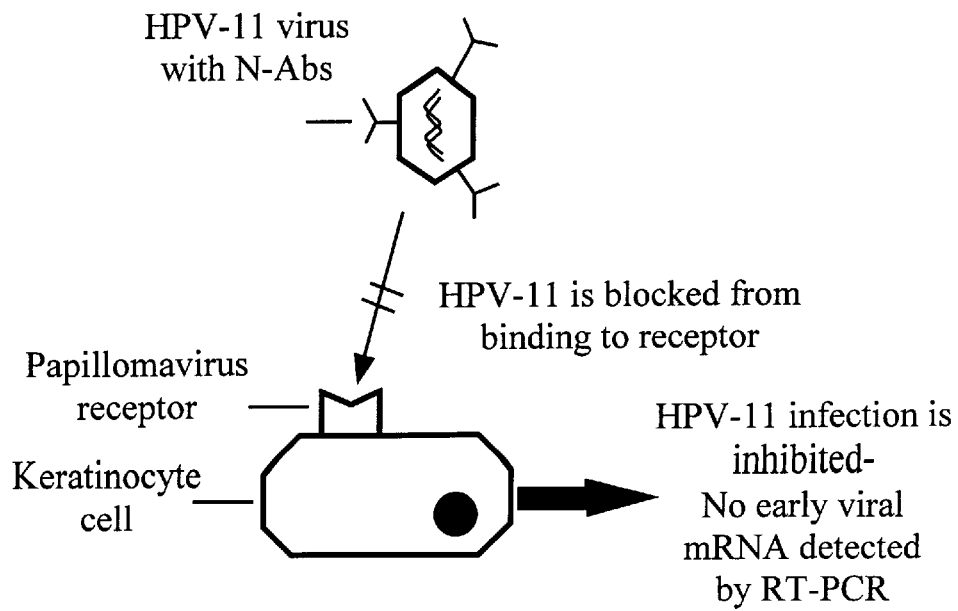
FIG. 1B is a diagrammatic depiction of the incubation of virion with antiviral agents prior to subjecting the cells to virus in accordance with the invention.

Referring more specifically to the drawings, for illustrative purposes the present invention is embodied in the method shown generally in FIG. 1 through FIG. 4. It will be appreciated that the method may vary as to detail and order of events without departing from the basic concepts as disclosed herein. The invention is disclosed generally in terms of use with HPV-11 virus. It will be readily apparent to those skilled in the art. however, that the invention may be used for identification of antiviral agents for various viruses, both human and non-human. Thus, the particular details disclosed herein should not be considered limiting.

The invention comprises generally growing cells in a multi-well format, infecting the cells with intact virion incubated with a test agent, and measuring expression of at least one viral nucleic acid sequence in said cells. The method also preferably comprises incubating intact virion without test agent to define a control. The cells are preferably human keratinocyte cells grown in monolayers. The viral nucleic acid sequence will generally comprise viral mRNA. In one preferred embodiment, the intact virion comprise Human Papilloma Virus, and more preferably Human Papilloma Virns -11. Measuring expression is generally carried out by releasing the viral mRNA from the cells by lysis, amplifying the mRNA as cDNA via RT-PCR, and detecting amplicons with specific probes. Cell lysis may be carried out by heating or by treatment with detergent. The details of carrying out the aforementioned events are provided by the following specific examples.

Preparation of HPV-11 Virus Stock

The Hershey strain of HPV-11 was utilized to generate xenografted condyloma tissues in athymic mice as described by Kreider et al., *J. Virol.* 61, (2) 590–593 (1987). HPV-11 virus extracts were purified by CsCl gradient. The purity of the preparation was in excess of 90% as judged by SDS-PAGE.

HPV-11 Infectivity and Neutralization Assay

HaCaT cells, an immortalized epithelial cell line derived from adult human skin were propagated in complete media and then plated into 96-well tissue culture plates at a density of $1\times10^4$ cells/well with Iscoves media with 2% fetal calf serum.

HPV-11 virion were added to the cells at varying dilutions of HPV-11 stock with an approximate concentration of $10^9$ virus particles/ml. To detect neutralizing antibodies, test serum was added to HPV-11 virion at varying concentrations prior to addition of virus to the keratinocytc cells. The infected cells (with and without neutralizing antibodies) were grown for four to eight days in serum-free media (154/HKGS, Cascade Biologics, Portland, Oreg.).

mRNA Cellular Release Without Organic Extraction or Purification.

Omitting the lengthy procedures necessary to organically extract RNA from cellular proteins and DNA, is an important time saving procedure for high throughput screening and is advantageous to other HPV in vitro infectivity assays.

mRNA Preparation Method 1: Trypsinization of tissue culture cells followed by heat lysis.

The keratinocyte cells are trypsinized (100 ul of 0.25 mg/ml trypsin w/o EDTA) for 30 min at 37° C. The trypsin was quenched by the addition of fetal calf serum (2% f.c.). The cells were transferred to a 96 well PCR plate and centrifuged for 5 min at 1350 rpm. The supernatant was removed and 100 ul of RNAase/DNAase free $H_2O$ or PBS was added to the cells. The cells could be stored at –80° C. or directly lysed by placing the PCR plate containing the cells in the thermal cycler for 5 min at 98° C. to release mRNA from the cells. After lysis, the samples are centrifuged at 2350 rpm for 4 min. 8 ul of lysis solution is added directly to the RT-PCR solution for amplification.

mRNA Preparation Method 2: Cellular lysis by detergent solution.

After keratinocyte cells grown to confluency in 96-well tissue culture plates, the cells are exposed to enough lysis solution (0.05% Lithium dodecyl sulfate, 50 mM TrisHCl pH7.4) to cover all the cells in the well (approximately 30 ul). The cells are lysed for 10–15 min at room temperature. 70 ul of water containing a RNase inhibitor is added to each well. This dilution step insures that the concentration of detergent is diluted sufficiently to not interfere with the reverse transcriptase and/or PCR polymerase enzyme acitivity in the RT-PCR reaction. Samples are centrifuged at 2350 rpm for 4 min. 8 ul of lysis solution is added directly to the RT-PCR solution for amplification. The lysed samples maybe stored at –80° C. for at least 11 months. This method of cell lysis is utilized for mRNA capture systems.

mRNA Preparation Method 3. Cellular lysis by detergent solution and subsequent mRNA capture.

mRNA preparation method 2 is utilized followed by mRNA capture. Cellular mRNA can be captured by either oligonucleotides of dT (20 mer) or the specific reverse HPV primer (3'end) which are attached via a biotin-streptavidin binding or a covalent linkage to the surface of the PCR tube in the presence of high salt concentrations (0.5 M NaCI). 50 ul to 100 ul of the lysed sample is incubated for 10 min to capture mRNA (with oligo dT) or mRNA/DNA (specific HPV primer). The samples are then washed with buffer (TrisHCI neutral pH) to remove detergent. The mRNA of interest is captured on the surface of the PCR tube and ready for solid phase RT-PCR.

Generation of HPV-11 E2 Amplicons by One-Tube Reverse Transcriptase-Polymerase Chain Reaction.

In order to use crude cellular lysis as an RT-PCR sample, the target mRNA must contain a intron/exon splice site so that the complementary DNA generated can be distinguished from genomic DNA.

Primer and Probe Design

The preferred primer design for this assay positions the forward and reverse primers on opposite sides of the intron/exon splice site. This allows for the preferential amplification of the smaller cDNA over the longer genomic DNA. The HPV E2 transcript RT-PCR products tested with this assay were at least 800 bases smaller then the genomic E2 DNA.

Another primer design technique which has been implemented in this assay was to design one of the primers over the splice site which allows it to only bind to mRNA/cDNA and not genomic DNA under stringent annealing conditions (maximum annealing temperature).

Depending on the detection method described below the primers were modified with biotin at the 5'-end for ELISA calorimetric detection system (detection method 2) or labeled with a fluorophore at the 5'-end for fluorescent detection (detection method 4).

When the primers utilized did not overlap the splice site, probes were designed to encompass this sequence. The fluorogenic probe utilized in the real-time RT-PCR experiment was 5'-6-FAM and 3'-TAMRA and covered the HPV-11 E2 splice at nucleotide base 847^2622.

RT-PCR One-Tube Systems

Both two enzyme and on enzyme RT-PCR systems have been tested for use in this high throughput HPV in vitro infectivity assay. Reaction conditions were optimized for the specific enzyems utilized.

Two enzyme RT-PCR system. HPV-11 mRNA along with a mRNA cellular internal control were amplified using the Promega Access RT-PCR system as described by Miller et al., *Promega Notes* 53,2 (1995). This one tube, two-enzyme system uses AMV reverse transcriptase (AMV RT) for first strand DNA synthesis and Tfl DNA polymerase for second strand cDNA synthesis and DNA amplification. $MgSO_4$ is utilized in the buffer system in place of $MgCl_2$ due to the specificity of Tfl polymerase. RNAasin, a RNAase inhibitor from Promega was also added to the RT-PCR mixture. The samples were incubated for 45 min at 48° C. for first strand cDNA synthesis, then heated to 94° C. for 2 min to denature the template.

One enzyme RT-PCR sytsem. For real-time RT-PCR, the one enzyme RT-PCR system by Perkin-Elmer rTth polymerase and EZ RF-PCR buffer system as described by the Perkin-Elmer Corporation, TaqMan EZ RT-PCR Kit Protocol, Foster City, Calif. The reverse transcriptase step was carried out at 63° C. for 30 min to optimize the reverse transcriptase activity of rTth polymerase and the heated to 94° C. for 2 min to denature the template. The sequence of the HPV probe (6-FAM/TAMRA) overlaps the E2 splice site to preferentially detect amplification of E2 cDNA and not HPV DNA.

PCR Reaction Condtions.

Template denaturation was carried out at 94° C. for 15 sec followed by an optimal temperature of 62° C. for primer annealing and extension. The longest extension time possible in which target cDNA was preferentially amplifed over genomic DNA was determined experimentally. RT-PCR products from runs with varying extension times (30 sec to 1 min) were analyzed by gel electrophoresis to determine the maximum extension time in which HPV DNA is not amplified due to its larger size. 45 to 50 cycles of PCR were found to be sufficient to detect E2 transcript RT-PCR products.

Detection of HPV-11 E2 Amplicons.

Method 1: Ethidium bromide/agarose gel electrophoresis.

The RT-PCR products (13 ul) were separated by electrophoresis on a 1.5% agarose gel with 0.05 ug/ml Ethidium bromide at 80 V for 30 min.

Method 2: ELISA Detection.

Amplified HPV-11 products (8 ul) were captured on a streptavidin coated 96-well plate in the presence of TBS pH 7.5, 0.1% BSA for 1 hr at 24° C. followed by a 15'min incubation in 150 mM NaOH to remove the unbound DNA strand. After NaOH denaturation, the wells were washed 4×3 with TBS 0.05% tween 20 (wash buffer).

Alkaline phosphatase Oligonucleolide probe. An alkaline phosphatase Oligonucleotide labeling kit from Boehringer Mannheim was utilized to couple alkaline phosphatase (AP) directly to an internal HPV-11 E2 oligonucleotide (22 base pairs), in the manner described by Joblonski et al., *Nucleic. Acids Res.* 14 (15), 61156129 (1986). The E2 specific AP-DNA probe (2 nM) was hybridized to the captured E2 amplicons in TBS for 1 hr at 42° C. Excess AP-DNA probe was removed by 5 washes. 100 ul of p-nitrophenyl phosphate was added to the wells, incubated for 2 hours in the dark and then read at 405 nm.

Digoxigenin labeled probe. The digoxigenin labeled probe for the E2 amplicons was produced by the incorporation of digoxigenin-11-2'-deoxyuridine-5'-triphosphate (10 uM) into E2 PCR products, utilizing primers internal to those used in the HPV infectivity assay as described by Galvan et al., *Clin. Bioch.* 30 (5) 391–397 (1997). . The DIG-probes were heated to 98° C. for 2 min and then quick cooled to produce single stranded DNA. 1 ul of probe was added to each will of captured E2 PCR products in TBS 0.05% tween 20 for 1 hr at 42° C. After incubation, the wells were washed 4× and AP-labeled anti-digoxigenin Fab fragments (1:2500 dilution) were added to the wells and incubated for 1 hour. After 5 washes, p-NPP was added to the wells, incubated for 15 min and read at 405 nm.

Method 3: Real-time RT-PCR.

This method utilized the ABI 7700 thermal cycler system. Unmodified primers for HPV-11 E2 and GAPDH transcripts are used along with a fluorogenic probe specifically designed for the HPV-11 E2 transcript (6-FAM/TAMRA) along with the fluorogenic probe for the GAPDII (JOE/TAMRA) supplied by Perkin-Elmer for real-time fluorescence detection of both the HPV-11 amplification and the internal control, GAPDH within the same PCR tube as described in the Perkin-Elmer Corporation, ABI 7700 Sequence detection system, bulletin #2, 1997, Foster City Calif.

Method 4: Fluorescence detection of HPV-11.

In this method modified primers are utilized for capturing amplicons and also for fluorescence detection. Reverse primers for HPV-11 and the internal control, GAPDH are modified at the 5'-end with biotin. Forward primers are modified with a fluorophore which is capable of with standing RT-PCR conditions. A forward HPV-11 5'-Cy5 modified primer and a 5'-Oregon Orange 488 modified GAPDH forward primer are utilized at present. RT-PCR conditions utilized are described above. RT-PCR products are captured on a streptavidin coated EIA plate, washed three times to remove unbound primer and 50 of buffer, either TBS or PBS (0.05% tween 20) is added to the wells. The samples are analyzed at two different excitation wavelengths, one blue and one red fluorescence on a molecular dynamics storm 860 instrument, as related by Molecular Dynamics Inc., "Fluorescence Imaging Applications Guide", 1996, guide #9621, Sunnyvale Calif.,94086-4520, U.S.A.

Discussion

This one tube, RT-PCR system provides sensitive, quick and reproducible analysis of rare RNAs. The utilization of less HPV virion makes this system applicable for the analysis of high risk HPV types which are not propagated in large quantities. The 96-well format enables the analysis of a large number of patient specimens which will be beneficial in the screening for protective immunity in ongoing clinical HPV vaccine trials as well as longitudinal studies on the HPV humoral immunity of patients with HPV related disease.

HPV-11 Virus Titration.

Figure 3A:
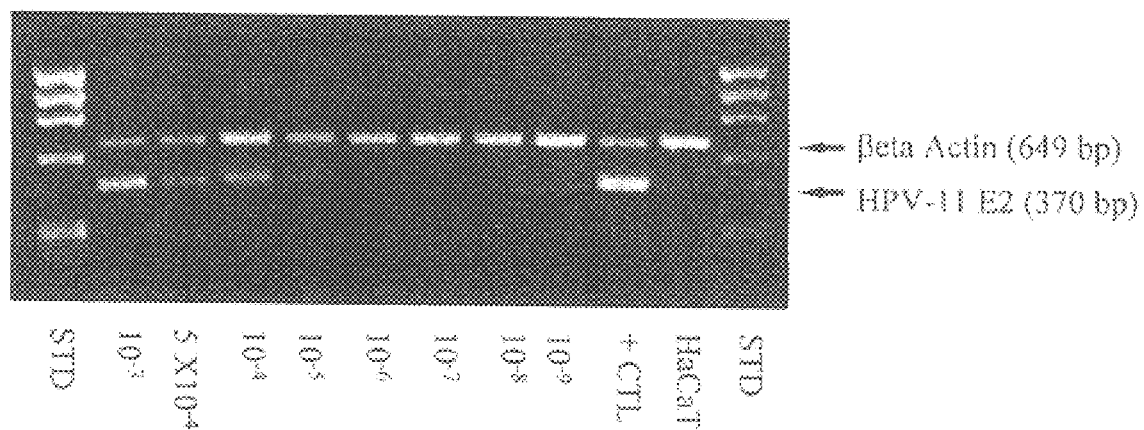
FIG. 3A illustrates gel electrophoresis wherein lanes 1 & 12-Φx-174/Hae III digest standard. Lanes 2–8 show RT-PCR products following serial dilution of HLP-11 infection in HaCaT cells; $10^{-3}$, $5\times10^{-4}$, $10^{-4}$, $10^{-5}$, $10^{-6}$, $10^{-7}$, $10^{-8}$, $10^{-9}$, with mouse condy positive control and uninfected HaCaT cells respectively shown in lanes 10 and 11.

Previous virus titration experiments utilizing the original HPV-11 in vitro infectivity assay could only detect the presence of HPV-11 mRNA when virus stock was diluted $5\times10^4$. This infectivity assay is capable of detecting infection at a viral dilution of $1\times10^5$ as shown in FIG. 3A. FIG. 3B shows the corrsesponding ELISA data for the titration samples in panel A after detection by hybridization to an alkaline phosphatase labelled E2 probe and addition of p-NPP. FIG. 3B also shows the Ct values (PCR cycle in which amplification of target is detected) for comparable results utilizing the real-time RT-PCR ABI 7700 system. The increased sensitivity of the HPV-11 in vitro assay coupled to these two detection systems demonstrates the detection of HPV-11 infectivity at a viral dilution of at least $1\times10^5$ without nested set PCR.

HPV-11 Neutralization Results for the Serum of Three Patients

Figure 4:
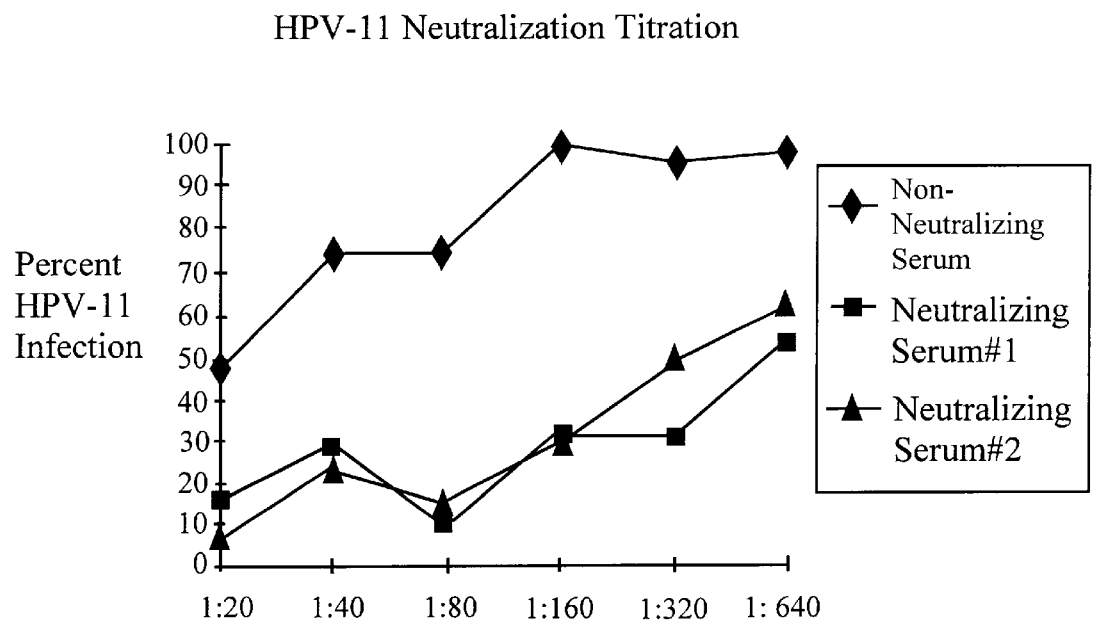
FIG. 4 is a graphic representation showing the RT-PCR products following serial dilutions of serum from three patients. The biotinylated RT-PCR HPV-11 E2 amplicons were captured on a streptavidin plate and hybridized with an alkaline phosphase-oligo probe specific for E2 followed by the addition of p-nitrophenyl phosphate substrate for colorimetric detection. Sera with HPV-11 infection percentages below 50% were determined to be neutralizing.

The following results are from the ELISA detection system, (detection method 2). Three patient sera were analyzed for the presence of HPV-11 neutralizing anitbodies. Varying concentrations of sera were incubated with HPV-11 virion before the addition of virus to keratinocyte cells. FIG. 4 represents the ELISA data utilizing the alkaline phosphatase E2 DNA for the detection of the presence of HPV-11 E2 mRNA. Two of the serum samples contain neutralizing antibodies which were detectable at a 1:640 dilution above HPV-11 viral controls. The other sera sample contains no neutralizing antibodies (decrease in the detection of E2 mRNA at 1:20 dilution is due to decreased cellular growth from the high concentration of sera).

The High-Throughput HPV-11 in vitro infectivity assay of the invention offers several advantages over previously available assays. The assay of the invention is adapted for high throughput screening throughout the procedure. Additionally, no mRNA isolation or purification is necessary for RT-PCR amplification and detection when using the present invention. Further, the present invention decreases the possibility of cross contamination by eliminating nested set PCR and also the need for separate reaction vessels for RT and PCR. Still further, the assay of the invention allows for quantitative analysis of HPV antiviral agents, in particular, neutralizing antibodies by eliminating nested set PCR and analyzing RT-PCR products with detection methods which allow numeric representation of the amount of RT-PCR amplification.

What is claimed is:

1. A high throughput detection method for mRNA comprising:
   (a) releasing crude nucleic acids from cells, said crude nucleic acids including at least one target mRNA having a splic site;
   (b) performing RT-PCR on said crude nucleic acids under an amplification condition which allows specific amplification of said target mRNA as cDNA while preventing amplification of other said nucleic acids; and
   (c) measuring amplification of said cDNA associated with expression of said mRNA.

2. The high throughput detection method of claim 1, wherein said amplification condition comprises:
   (a) using a first, forward primer positioned on a first side or a splice site associated with said target mRNA; and
   (b) using a second, reverse primer positioned on a second side of said splice site.

3. The high throughput detection method of claim 1, wherein said amplification condition comprises an eclongation time sufficient to amplify said cDNA and not other said nucleic acids of greater length than said cDNA.

4. The high throughput detection method of claim 1, wherein said mRNA is derived from cells which are grown in monolayers.

5. The high throughput detection method of claim 1, wherein said mRNA comprises viral mRNA.

6. The high throughput detection method of claim 1, wherein said releasing of said crude nucleic acids comprises lysis of said cells.

7. The high throughput detection method of claim 1, wherein said measuring of said amplification of said cDNA further comprises detecting amplicons from said RT-PCR according to interaction of said amplicons with a nucleotide probe specific for said amplicons.

8. The high throughput detection method of claim 5, wherein said viral mRNA is Human Papilloma Virus mRNA.

9. The high throughput detection method of claim 8, wherein said Human Papillorna Virus mRNA is Human Papilloma Virus -11 mRNA.

10. The high throughput detection method of claim 6, wherein said lysis of said cells is carried out by heating said cells.

11. The high throughput detection method of claim 6, wherein said lysis of said cells is carried out by treating said cells with detergent.

12. A method for detecting a target mRNA from an unpurified cell lysate, said method comprising:
   (a) lysing cells to form a crude lysate, said crude lysate including genomic DNA and said target mRNA, said target mRNA having a splice site;
   (b) carrying out RT-PCR on said crude lysate using an extension time which preferentially forms amplicons of cDNA associated with said target mRNA, and not of said genomic DNA; and
   (c) detecting said amplicons of said cDNA.

* * * * *